United States Patent [19]

Grigereit

[11] Patent Number: 5,234,339
[45] Date of Patent: Aug. 10, 1993

[54] IMPLANT SUPPORTED PROSTHESIS

[75] Inventor: Helmut Grigereit, Laguna Niguel, Calif.

[73] Assignee: Kulzer, Inc., Irvine, Calif.

[21] Appl. No.: 814,070

[22] Filed: Dec. 24, 1991

Related U.S. Application Data

[63] Continuation of Ser. No. 655,310, Feb. 14, 1991, abandoned.

[51] Int. Cl.⁵ .................. A61C 13/12; A61C 8/00; A61C 13/225
[52] U.S. Cl. .................................. 433/172; 433/173; 433/180
[58] Field of Search ............... 433/171, 172, 173, 174, 433/177, 181, 180

[56] References Cited

U.S. PATENT DOCUMENTS

| | | | |
|---|---|---|---|
| 709,410 | 9/1902 | Kelly | 433/172 |
| 4,084,318 | 4/1978 | McEachern | 433/174 |
| 4,204,321 | 5/1980 | Scott | 433/177 |
| 4,318,742 | 3/1982 | Lokken | 106/35 |
| 4,378,248 | 3/1983 | Griffith | 106/35 |
| 4,600,390 | 7/1986 | Göbel et al. | 433/218 |
| 4,620,988 | 11/1986 | Garschke et al. | 427/223 |
| 4,931,016 | 6/1990 | Sillard | 433/172 |
| 4,980,391 | 12/1990 | Kumar et al. | 524/45 |
| 4,986,753 | 1/1991 | Sellers | 433/172 |
| 5,000,685 | 3/1991 | Brajnovic | 433/173 |
| 5,092,771 | 3/1992 | Tatum, III | 433/173 |
| 5,100,323 | 3/1992 | Friedman et al. | 433/173 |

FOREIGN PATENT DOCUMENTS

| | | |
|---|---|---|
| 288446 | 10/1988 | European Pat. Off. . |
| 296513 | 12/1988 | European Pat. Off. . |
| 466267A1 | 1/1992 | European Pat. Off. . |

Primary Examiner—Gene Mancene
Assistant Examiner—Cindy A. Cherichetti
Attorney, Agent, or Firm—Graham & James

[57] ABSTRACT

An implant supported prosthesis, and a method for making an implant supported prosthesis, including a framework cast from a wax-up frame, at least one implant abutment, a fixation means for securing at least one abutment to the mouth and at least one cylinder securely attachable to each of the at least one abutments. The framework is cast including the casting of surfaces defining at least one aperture. The framework is mounted in the mouth with the at least one aperture receivably mating with the at least one cylinder. The framework may then be bonded onto the at least one cylinder by use of a luting material.

18 Claims, 3 Drawing Sheets

IMPLANT SUPPORTED PROSTHESIS

This is a continuation of copending application Ser. No. 07/655,310, filed on Feb. 14, 1991, now abandoned.

FIELD OF THE INVENTION

This invention relates generally to dental implants and, more particularly, to a novel implant supported prosthesis and method for making an implanted supported prosthesis.

BACKGROUND OF THE INVENTION

Fixed restorative treatments are commonly used to arrest a deteriorating dental condition. In fact, increased lifestyle demands of the aging general population has resulted in an increasing number of patients seeking fixed restorative treatment for the undermined cosmetics and function that frequently accompany a deteriorating dental condition. One such treatment sought is a dental implant supported prosthesis.

Dental implants are well known in the art and restorative techniques currently used for pre-fabricated devices were developed many years ago, between 1930 and 1950. The restorative techniques used for implant supported restorations are not fundamentally different from the techniques used for the restoration of natural tooth abutments. Briefly, the present customary practice for making a metal framework for an implant supported prosthesis involves making a stone model from the patients mouth, including the simulation of the implants by use of analogues and placing metal cylinders on these analogues. A wax model is then made integrating the metal cylinders and this wax model is lifted off from the stone model and invested and cast. Accordingly, the cylinders are an integrated part of the framework. The framework is completed with gingival tissue simulating material and artificial teeth and the framework is securely seated in the patients mouth by the cylinders being placed over and securely attached to the dental implant abutments. The implant abutments are previously implanted into the patients mouth The dental implant abutment, however, raises several concerns, many of which are not material in natural tooth abutments. Implant abutments obviously lack the periodontal ligament complex located around natural teeth. The absence of periodontal ligaments precludes the implant abutment from moving within the stomatognathic system to the same degree as natural abutment teeth. Existing implant abutments, as described briefly above, may introduce unacceptably high stresses into the bone-implant-abutment complex because of undetected frame-to-implant fit discrepancies. This stress may result in the loosening of fixation screws, stress induced resorption of bone and, ultimately, failure of the implant.

Because existing restorative techniques and systems use impression or model and die systems, inconsistent volumetric and linear expansion are frequently manifested during seating of the framework. This expansion results in the creation of unacceptably high tension on abutment teeth and implant abutment components. Vertical dimensional changes are also not uncommon in existing implant restorations and often result in insufficient abutment to restoration contact area.

Additionally, standard laboratory techniques of casting the implant framework from a stone model of the mouth do not permit the high volume fabrication of single-unit cast frameworks to a high degree of accuracy. This is because the tolerances between the second generation cast based on the stone model and the actual measurable fit dimensions of the mouth are unacceptably high. Thus, in multiple abutment situations the high volume castings of existing restoration systems often require dividing them into several segments in order to achieve an acceptable fit. These segments are then soldered together before placement in the mouth and attachment to the implant abutment. This segment casting method necessitates labor intensive and technique sensitive soldering operations. Accuracy levels vary dramatically after soldering the segment castings together and subsequently substantial time is required to finalize the implant restoration fit.

SUMMARY OF THE INVENTION

It is therefore desirable and an object of the present invention to provide an implant supported prosthesis, and a method for making an implant supported prosthesis, that reduces the restorative work induced stresses often present in the bone-implant-prosthesis system. It is another object of the present invention to minimize the technical sensitivity of clinical and laboratory procedures involved in making and implantation of an implant supported prosthesis.

It is still another object of the present invention to provide an implant supported prosthesis, and a method for making an implant supported prosthesis, with improved aesthetics. It is yet another object of the present invention to provide an implant supported prosthesis, and a method for making an implant supported prosthesis, that minimizes the presence of harmful galvanic reactions when introduced into the stomatognathic system. And, it is a still further object of the present invention to provide an implant supported prosthesis, and a method for making an implant supported prosthesis, having multiple implant abutments and the absence of structural weakening soldering joints.

Generally stated, the present invention of an implant supported prosthesis, and a method for making an implant supported prosthesis, includes making a stone model from the patient's mouth and including the simulation of implant abutments by the use of analogues. Cylinders are also placed on the analogues. A wax frame-up model is made from the stone model and this wax model is lifted off from the stone model. Abutments are previously implanted into the gingival tissue and cylinders passively seated thereon. The wax model is invested and casted, including the casting into the framework of surfaces defining apertures. The apertures correspond to each of the analogue simulated implant abutments and cylinders. A resin layer is applied to the framework and the framework is positioned inside the mouth. The apertures cast into the framework are engaged with the implant abutment mounted cylinders, the cylinders passing up into the framework apertures. The framework is then bonded to the cylinders with a composite luting cement and the prosthesis completed with gingival tissue simulating material and artificial teeth.

It is believed that a better understanding of the present invention, as well as a recognition of how the present invention achieves the foregoing objects and attains various additional advantages, will become apparent to those sufficiently skilled in the art from a consideration of the following detailed description of the present invention. During the following detailed description, reference will be made to the appended sheets of drawings that are described briefly immediately below.

DETAILED DESCRIPTION OF THE DRAWINGS

Figure 1:
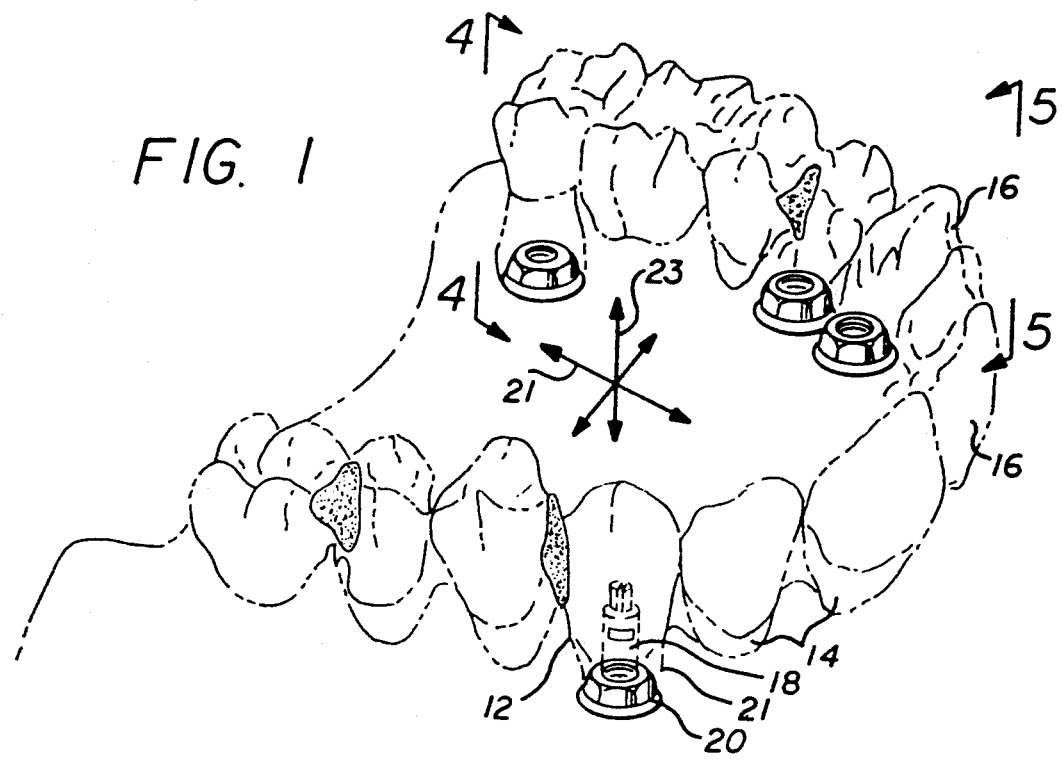
FIG. 1 is a side-perspective view of a maxillary implant supported dental prosthesis in accordance with the present invention.

Preliminarily, to facilitate an understanding of the present invention, the prosthesis environment will be briefly discussed in connection with FIG. 1. FIG. 1 is a side-perspective view of a maxillary implant supported dental prosthesis in accordance with the present invention. The implant supported prosthesis is generally indicated as 10. The prosthesis 10 includes a framework 12 completed with gingival tissue simulating material 14 and artificial teeth 16. The prosthesis 10 is supported by abutments 18 and fixation screw systems 20 (as shown in shadow on FIG. 1). It should be understood that the method of making completed prosthesis 10 of FIG. is such that the framework 12, abutments 18, fixation screw system 20 and related structural members of prosthesis 10 are not visually apparent from outside the mouth. The framework 12 and related structural members of prosthesis 10 are hidden by gingival tissue simulating material 14 and artificial teeth 16.

While fixation screw systems 20 are typically used to secure abutments 18 to the implanted fixture 21, any means may be used to secure the abutments 18, and attached framework 12 of prosthesis 10. By way of example, but not of limitation, fixation screw system 20 may be replaced by a clip system or a magnet system.

It is contemplated that the present invention of an implant supported prosthesis 10 encompasses both a tissue supported and an osseointegrated prosthesis. An osseointegrated implant has a direct structural and functional connection between ordered living bone and the surface of the artificial load-carrying implant.

It should also be understood that while the number of abutments 18 may vary, the method of making the prosthesis 10 is not impacted. Further, additional abutments 18 are not required solely for strength of the implant prosthesis 10. As was discussed in the Background Of The Invention, prosthesis 10 is subjected to a number of forces when implanted into the stomatognathic system. The forces exerted upon prosthesis 10 do not fall solely within the X-Y Plane and angular forces may be exerted in any direction. For purposes of illustration, directional arrows 21 and 23 show the volumetric and linear expansion that must be both tolerated and compensated for by prosthesis 10.

Tension on abutment teeth or implant abutment components (as shown by directional arrow 21) caused by framework 12 can approach the 50-200 micron range. Vertical dimensional changes (shown by directional arrow 23) often are expressed as infra- or supra-occlusal contacts and insufficient abutment to restoration contact area. As is discussed within, the implant supported prosthesis 10 of the present invention compensates for both the natural, and surgeon created, recesses and fit discrepancies that would otherwise exert undesirable stresses upon implant supported prosthesis 10. The construction of prosthesis 10 is best shown in connection with FIGS. 2-5, which are addressed immediately below.

Figure 2:
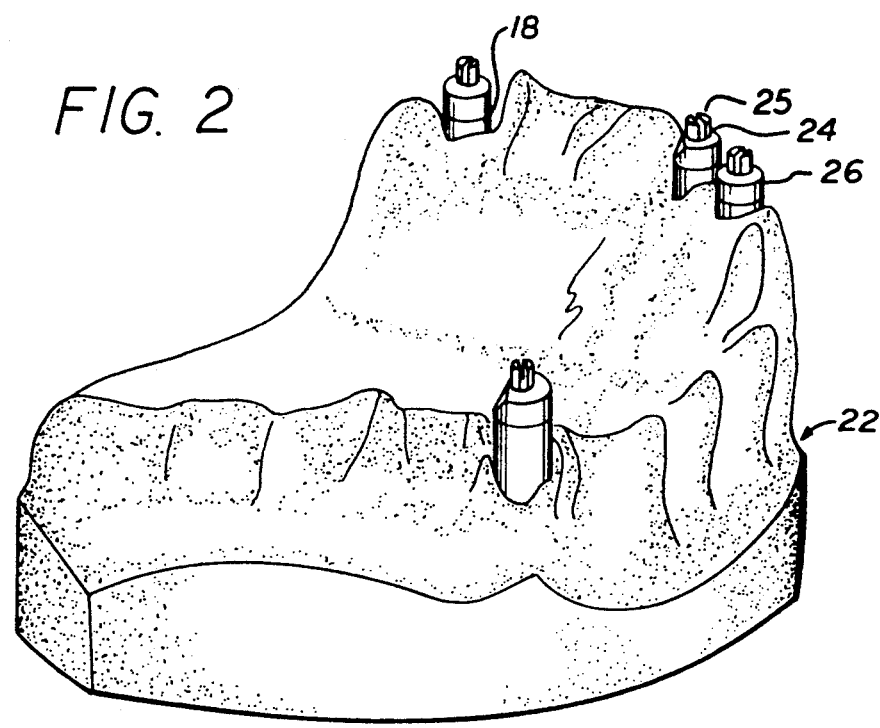
FIG. 2 is a side-perspective view of a stone model of a patients mouth as utilized in making an implant supported dental prosthesis in accordance with the present invention.

Turning, then, to FIG. 2, FIG. 2 is a side-perspective view of a stone model of a patient's mouth as utilized in one of the steps in making implant supported dental prosthesis 10 in accordance with principle of the present invention. Stone cast model 22 of FIG. 2 shows implant analogues 24. Implant analogues 24 serve to simulate the implant abutment 18 and a cylinder 26 attached to the implanted fixture 25. Implant analogues 24 also depict the utilization of a fixation screw 25. It is from the stone model 22 with implant analogues 24 that framework 12 is cast.

Addressing implant analogues 24 in greater detail, implant analogue 24 is shown in FIG. 2 to have abutment 18 and cylinder 26. Cylinder 26 is the upper portion of implant analogue 24 and comes in contact with framework 12. For purposes of casting framework 12, implant analogues 24 may be made up of most any metal or plastic material. As is discussed within in connection with FIG. 5, the material composition choice for actual implantation must take into consideration various biological factors, e.g., galvanic reactions. For illustration purposes, it is common to make cylinder support 26 out of gold. The gold cylinder support 26 is incorporated into the final restoration and provides the interconnection of framework 12 to abutment implant 18.

It should be clear from FIG. 2 that it is not always possible to locate abutments 18 in the ideal tooth position. The implanting surgeon may be faced with constructing implant supported prosthesis 10 with abutments 18 located lingually or buccally to the desired tooth position. It is not uncommon for abutments 18 to be properly attached to the implanted fixture system 20 and nonetheless have a significant angular orientation. Improper implant placement, however, can result in a framework design that compromises both aesthetics and the distribution of forces on implants. FIG. 2 includes only implant analogues 24. It is within the scope of the present invention that framework 12 may be utilized with a dentureless patient, as shown in FIG. 2, or with natural tooth abutments.

By way of example with respect to the angulation of abutments 18, distal inclination of fixtures may result from the natural lingual concavity of the mandible. Additionally, certain distal inclination may occur from the placement of the abutment fixture when the implanting surgeon has the mandible open. At such a time, it is not uncommon for the angulation of the abutment fixtures 18 relative to the occusal plane to be slightly misjudged. While it is obviously preferable to achieve the optimal angulation of the fixtures at the correct vertical dimension of occlusion, this often involves some prospective anticipation by the surgeon. The present invention allows for the innate imperfection of the implant angulation.

Figure 3:
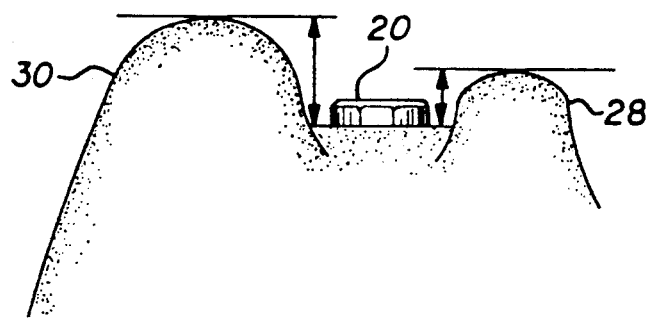
FIG. 3 is a partial cross-sectional view of a patients mouth with a passively seated screw assembly implanted abutment.

As discussed in connection with FIG. 2, proper fitting of the abutments 18 is essential for a successful prosthesis 10. FIG. 3 is a partial cross-sectional view of a patient's mouth with a passively seated screw assembly 20 implanted. Tissue thickness of the gingival wall varies from lingual (generally indicated at 28) and labial (generally indicated at 30) as well as from location to location in the arch. To minimize the buccolingual width of the prosthesis 10, as well as the neutral space required for cylinders 26, the framework 12 is typically thinned. While such thinning can weaken the framework 12, the prosthesis 10 of the instant invention compensates for such buccolingual variance by utilization of a bonding material (discussed below in connection with FIG. 5). Angular discrepancies of the abutment fixtures 18 are also tolerated by framework 12 of the prosthesis 10 of the instant invention whereas in the existing known prosthesis such angulation can significantly complicate successful restoration. The advantages of framework 12 are best illustrated in connection with FIGS. 4 and 5.

Figure 4:
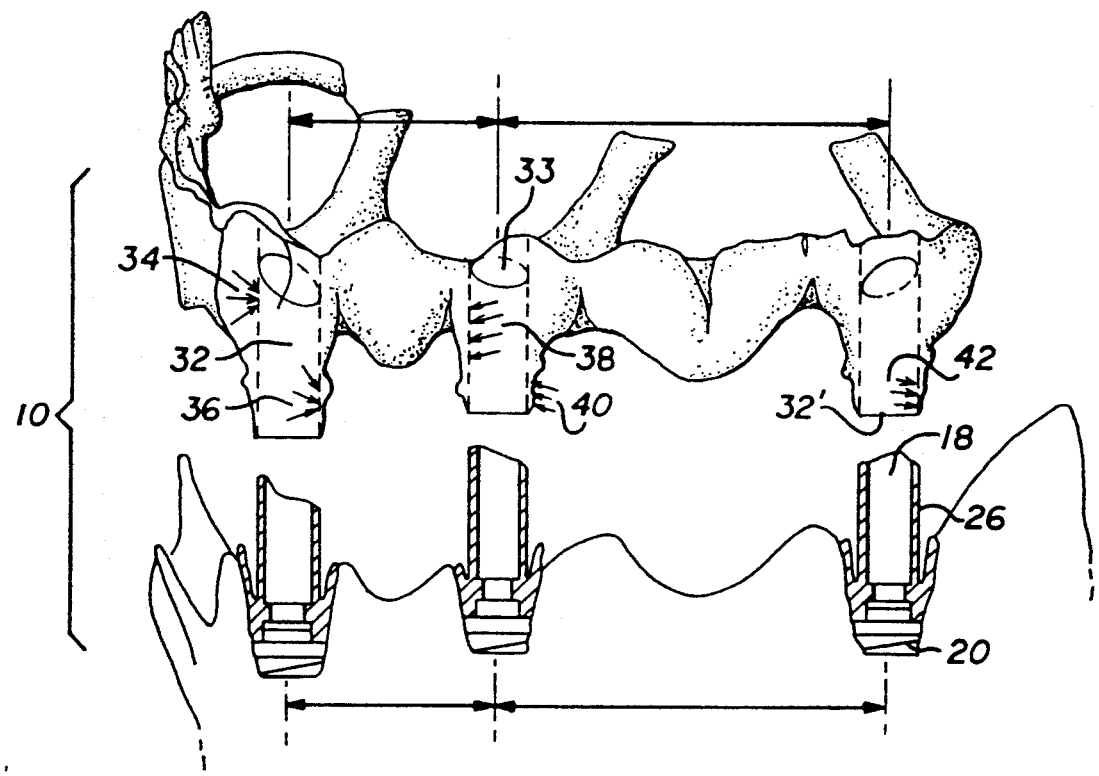
FIG. 4 is a partial exploded cross-sectional view taken through Plane 4—4 of FIG. 1 of an implant supported dental prosthesis made in accordance with the present invention.

Turning now to address FIG. 4, FIG. 4 is a partial exploded view taken through Plane 4—4 of FIG. 1 of implant supported dental prosthesis 10. Framework 12 has surfaces defining at least one aperture 32. Apertures 22 are created when framework 12 is cast and have a diameter greater than that of cylinders 26. Because cylinders 26 have a diameter that is smaller then the diameter of apertures 32, framework 12 may easily slide into position over abutment mounted cylinders 26.

The framework 12 is positioned over the abutment mounted cylinders 26 and this single unit cast frame is then adjusted, if necessary, to passively fit. By way of example, adjustment arrows 34, 36, 38, 40 and 42 show how the frame may be adjusted without altering the fit of any single abutment. Framework 12 may be machined for adjustment where necessary and the present invention allows for up to a millimeter of fit tolerance. For example, adjustment arrow 42 indicates how aperture 32 may be machined to a funicular shape without exceeding acceptable fit tolerances. These modifications may be made to apertures 32 by working directly on framework 12 when it is disengaged from cylinders 26. Thus, there is no stress or torque placed on the actual implanted abutments 18 or fixation system 20 during the fitting phase.

The single unit framework eliminates the necessity of single unit casting into a plurality of casting segments when working with multiple abutments. The old casting segment method requires the soldering of parts which is undesirable for two reasons. First, the framework itself can possibly be warped due to the high temperatures being applied during soldering. Second, the soldering adds an additional step to the making of the implant framework and imposes significant time and technical burdens upon the surgeon or laboratory technician.

It should be appreciated that once framework 12 is positioned over cylinders 26 and implant abutment 18, there will be certain surfaces and recesses having openings. These recesses may be created, for example, by the need to alter apertures 32 to ensure a passive seating or, by further example, due to distal inclination. Framework 12 is bonded to the cylinders 26 and implant abutments 18 in order to eliminate the surface openings and recesses. This bonding is achieved by introducing a luting material 52 into contact with framework 12. The luting material 52 compensates for and fills any openings or recesses that are created. The bonding process is best shown in connection with FIG. 5 and is addressed below.

Figure 5:
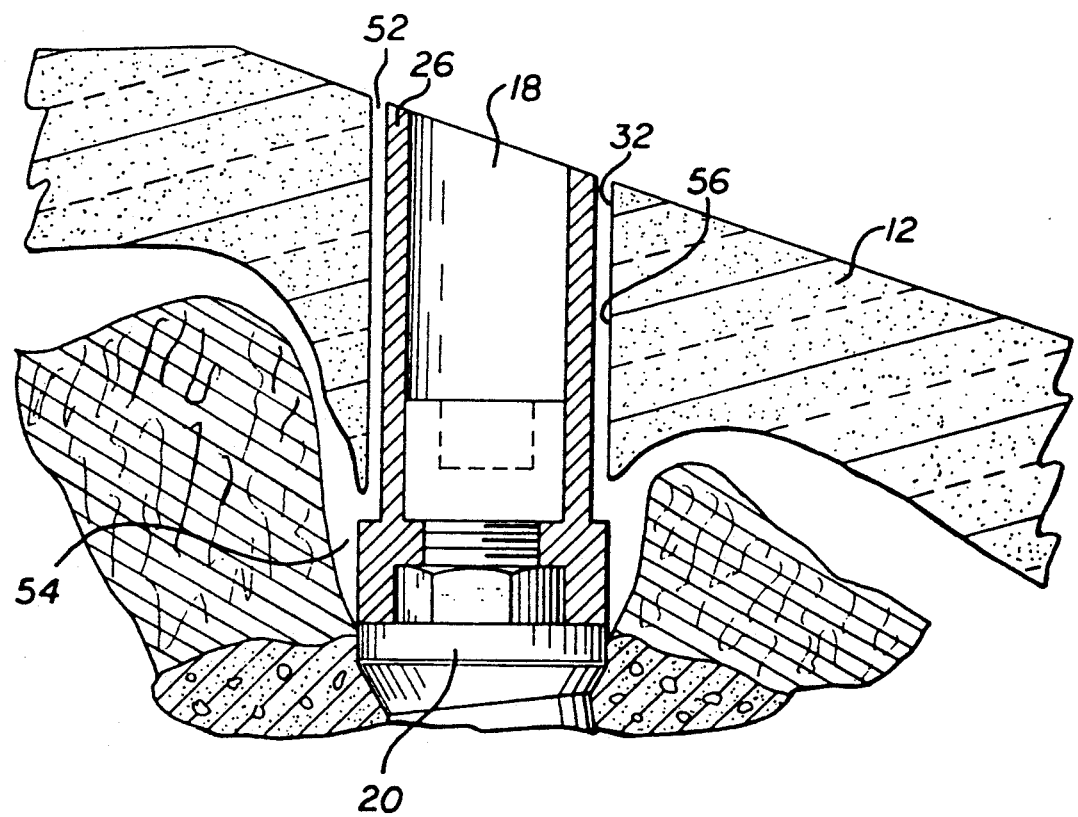
FIG. 5 is a cross-sectional view taken through Plane 5—5 of FIG. 1 of an implant supported dental prosthesis made in accordance with the present invention.

FIG. 5 is a cross-sectional view taken through Plane 5—5 of FIG. 1 and shows framework 12 secured to cylinders 26 by luting material 52. The liquid consistency of luting material 52 allows luting material 52 to flow and penetrate into small and otherwise inaccessible retention recesses, e.g., 54 and 56. By way of example, but not of limitation, FIG. 5 shows the manner in which retention recess is filled by luting material 52. It should be appreciated that luting material is flexible and thus will also absorb stresses imparted to prosthesis 10. The absorption of stress by luting material 52 avoids damage to either the natural tooth or framework 12.

The bonding step may be performed either before or after the finished, veneered restoration, e.g., gingival tissue simulating material 14 and artificial teeth 16, is attached to framework 12. If bonding is performed prior to completion of the restoration, fixation screw 25 is removed after bonding and the framework 12 and attached (by the bonding step) cylinders 26 are lifted off before the veneering is in turn completed. For example, in resin restorations luting may be, done with the framework 12 in place. In contrast, when working with porcelain restorations it is preferable to perform the luting step last because of temperature requirements of the porcelain restoration.

The bonding step may be performed so as to make the luting material, by either configuration or actual composition, the weak link of prosthesis 10. The purpose of this weak link is to protect other parts of prosthesis 10 from damage when subject to various stresses or force. The luting material 52 of the instant invention is designed so that it is the controlled weak link of prosthesis 10.

By way of further advantage, luting material 52 also provides an insulation between the metallic surface of framework 12 and cylinder surface 26 and abutment implant 18. It is important to avoid the contact of metals in the stomatognathic system because of the potential detrimental impact and effect of galvanic reactions. It should be noted that in the preferred embodiment both cylinders 24 and framework 12 are precoated with a chemical substance to minimize any potential galvanic reaction. By way of example, but not of limitation, such a coating may be silicon oxide-containing adhesion-promoting layer.

Material commonly used for an implant supported prosthesis are precious metal alloys, e.g., silver palladium. Precious metal alloys are strong and also cast well to the gold cylinders. Moreover, where in the prior art prosthesis soldering cast segments is required, precious metal allows are a preferred material because of its high melting point. It should be understood that because the instant invention eliminates the need for an segment casting and soldering, the range of materials that may be utilized may be increased where materials that otherwise meet the requisite biomedical and biomaterial characteristics of prosthesis 10 are left not utilized for the lack of a sufficiently high melting point or galvanic reaction.

Having thus described a preferred exemplary embodiment of the implant supported prosthesis of the present invention and a method for making the implant supported prosthesis in accordance with the principles of the present invention, it should be apparent to those skilled in the art that various additional objects and advantages have been attained by the within invention and that a variety of modifications can be made within the scope and spirit of the present invention, being limited only by the following appended claims.

I claim:

1. An implant supported dental prosthesis, said prosthesis comprising:
    (a) a framework;
    (b) at least one implant abutment;
    (c) fixation means for securing said at least one implant abutment to the mouth;
    (d) cylindrical mounting means securely attached to said at least one implant abutment for covering said implant abutment, said cylindrical mounting means having an outer diameter;
    (e) compensating orifice means positioned on said framework for receivably mating with said cylindrical mounting means, said orifice means having an inner diameter greater than the outer diameter of said cylindrical mounting means, the receivable mating thereby defining a generally cylindrical void;
    (f) flexible bonding means for receivably affixing said framework to said mounting means and for transmitting all stress forces therebetween, said flexible bonding means including luting material means for resiliently affixing said inner diameter of said orifice means of said framework to said mounting means and for filling said generally cylindrical void and all retention recesses.

2. The implant prosthesis as defined in claim 1 wherein said fixation means comprises a fixation bracket implanted into the tissue of said mouth and a screw assembly.

3. The implant as defined in claim 2 wherein said cylindrical mounting means includes at least one cylinder removably affixed to said at least one abutment.

4. The implant as defined in claim 4 wherein said compensating orifice means include surfaces defining at least one aperture.

5. A method of implanting a prosthesis in a mouth, comprising the steps of:
    implanting at least one implant abutment into the mouth, said at least one abutment secured in the mouth by utilization of a fixation means for securing said implant abutment to bone structure in the mouth;
    securely attaching a cylinder to each of said at least one implant abutments;
    casting a framework, said framework cast to include surfaces defining at least one aperture in a position corresponding to each of said at least one cylinder attached to said implant abutments;
    applying an adhesion promoting resin layer to said framework;
    mounting said framework in said mouth by receivably mating each of said at least one aperture with a corresponding cylinder; and
    bonding said framework to said cylinder.

6. The method as defined in claim 5 wherein said bonding includes luting material means for resiliently affixing said framework to said cylinder and for filing retention recesses.

7. The method as defined in claim 6 wherein said luting material means is a shock-absorbing adhesive material.

8. The method as defined in claim 6 wherein said luting material means is operative for providing a controlled weak link protecting said at least one implant abutment from damage caused by stress or force applied to said prosthesis.

9. The method as defined in claim 5 wherein said cylinder is a screw house.

10. A method for making and implanting a prosthesis in a mouth, comprising:
    making a stone model of the mouth and including the simulation of at least one implant abutment on said model by the use of at least one analogue;
    creating a wax frame-up model from said stone model;
    casting a single-unit framework from said wax frame-up model, said framework including compensating orifice means corresponding to said analogue for defining at least one aperture;
    implanting a least one abutment into the mouth;
    applying a resin layer to said framework, said resin layer being an adhesive-promoting layer;
    passively seating a cylinder on said at least one implant abutment;
    mounting said framework in said mouth by receivably mating said at least one compensating orifice means to said at least one cylinder;
    bonding said framework to said cylinder by use of a luting material means for resiliently affixing said framework said cylinders and for filling retention recesses.

11. The method as defined in claim 10 comprising the further step of attaching a finished veneered restoration to said framework.

12. An implant supported prosthesis comprising:
    (a) at least one implant abutment;
    (b) a framework;
    (c) means for attaching said framework onto said implant abutment and for simulating the flexible resilience of the natural periodontal ligament complex, wherein the only materials which simulate the flexible resilience and accommodate the transfer of stress from said framework to said abutment are luting and bonding materials.

13. The implant supported prosthesis as defined in claim 12 wherein said means for attaching includes:
    a mounting means securely attached to each of said at least one implant abutments for passively mounting said framework on said at least one abutment;
    at least one orifice means located on said framework in a position corresponding to each of said at least one mounting means for receivably mating with each of said at least one mounting means;
    bonding means for affixing said framework to said at least one mounting means.

14. The implant supported prosthesis as defined in claim 13 wherein said bonding means includes luting material means for resiliently affixing said framework to said at least one mounting means and for filling retention recesses.

15. A method for making and implanting a prosthesis in a mouth, comprising:
    making a stone model of the mouth and including the simulation of at least one implant abutment on said model by the use of at least one analogue;
    creating a wax frame-up model from said stone model;
    casting a single-unit framework from said wax frame-up model, said framework including compensating orifice means corresponding to said analogue for defining at least one aperture;
    implanting at least one abutment into the mouth;

passively seating a cylinder on said at least one implant abutment;

mounting said framework in said mouth by receivably mating said at least one compensating orifice means to said at least one cylinder;

bonding said framework to said cylinder by use of a luting material means for resiliently affixing said framework said cylinders and for filling retention recesses.

16. The method according to claim 15, further comprising applying a resin layer to said framework.

17. The method according to claim 16 wherein said resin layer is an adhesion-promoting layer and said luting material is a composite luting cement.

18. The method according to claim 15 wherein said luting material is a composite luting cement.

* * * * *